United States Patent [19]

Rakhit et al.

[11] Patent Number: 5,627,194

[45] Date of Patent: May 6, 1997

[54] ANTI-VIRAL GUANIDINO-SUBSTITUTED COMPOUNDS

[75] Inventors: Sumanas Rakhit; Abdelmalik Slassi, both of Mississauga, Canada

[73] Assignee: Allelix Biopharmaceuticals Inc., Mississauga, Canada

[21] Appl. No.: 322,492

[22] Filed: Oct. 14, 1994

Related U.S. Application Data

[63] Continuation-in-part of Ser. No. 153,981, Nov. 17, 1993, abandoned.

[51] Int. Cl.[6] .................. A61K 31/35; A61K 31/38; A61K 31/445; A61K 31/17
[52] U.S. Cl. .................. 514/315; 514/432; 514/459; 514/460; 546/247; 546/243; 549/13; 549/28; 549/417; 549/419; 564/236
[58] Field of Search ................ 549/13, 28, 417, 549/419; 564/236; 546/247, 243; 514/315, 432, 459, 460

[56] References Cited

U.S. PATENT DOCUMENTS 2,557,560  6/1951  Peck .................................. 564/57
3,468,898  9/1969  Cutler et al. ...................... 548/211

FOREIGN PATENT DOCUMENTS

WO9207871  5/1992  WIPO.

OTHER PUBLICATIONS

Hine et al., "Octakis–O–(3–aminopropyl) sucrose as a Bifunctional Catalyst for the Dedeuteration of Isobutyraldehyde-2-d[1]", J. Org. Chem., vol. 39, No. 22 (1974), pp. 3231–3236.

Nicolalou et al., "Design and synthesis of a peptidomimetic employing β–D–glucose for scaffolding", Peptides: Chem Structure Biol., 11th An Pepetide Symp. (1990), pp. 881–884.

Shankar et al., "A novel application of benzotriazole methodology: reactions of polyhydroxylated bis–(benzotriazoyl) piperidines with mono and bidentate nucleophiles", Tetrahedron Letters, vol. 34, No. 45, (1993), pp. 7171–7174.

*Primary Examiner*—S. Mark Clardy
*Assistant Examiner*—Mary C. Cebulak
*Attorney, Agent, or Firm*—Foley & Lardner

[57] ABSTRACT

Novel guanidino-substituted compounds are described having the following general formula (I):

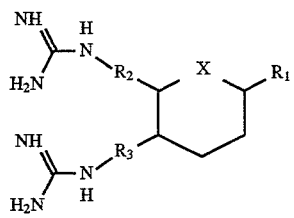

in which X may be carbon, oxygen, nitrogen or sulfur; $R_1$ may be H, OH, linear or branched lower alkyl, lower alkoxy, lower (alkyl-substituted alkoxy), lower alkyl-amine, lower alkyl-thio, hydroxy substituted lower alkoxy, lower alkoxy-alkoxy substituted lower alkoxy, hydroxy substituted lower alkyl-amine, alkoxy substituted lower alkyl-amine and terminally guanidino-substituted linear of branched lower alkyl, lower alkoxy, lower (alkyl-substituted alkoxy), lower alkyl-amine or lower alkyl-thio; and $R_2$ and $R_3$ are independently one of linear or branched lower alkyl, alkoxy, alkyl-substituted alkoxy and alkylamine.

These compounds have been found to inhibit effectively herpesvirus replication. Particularly preferred compounds in accordance with formula (I) for this purpose are guanidino-substituted sugar derivatives.

19 Claims, 7 Drawing Sheets

R = (CH$_2$)$_5$NHC(NBoc)NHBoc

A: 1) Et$_3$N, DMF, rt 15MIN 2) (BocNH)$_2$CS, rt 12HRS (83%)
B: Br$_2$, Ph$_3$P, CH$_2$Cl$_2$, 0°C→rt 4HRS (84.7%)
C: KOH (POWDER), THF, 18-CROWN-6 CAT, Br(CH$_2$)$_5$NHC(NBoc)NHBoc, rt 2HRS (78.5%)
D: H$_2$, Pd/C (10%), EtOAc, rt 2HRS (86.9%)
E: 3N. HCl, EtOAc, rt 2HRS (25%)

R = (CH$_2$)$_3$NHBoc
R$^1$ = (CH$_2$)$_3$NH$_2$
R$^2$ = (CH$_2$)$_3$NHC(NBoc)NHBoc

A: BF$_3$·Et$_2$O, 2-(2-ETHOXY ETHOXY)ETHANOL, BENZENE, rt 45MIN (85.7%)
B: NaOMe/MeOH, rt 12HRS (75%)
C: KOH (POWDER), THF, 18-CROWN-6 CAT, Br(CH$_2$)$_3$ NHBoc, rt 2HRS (45%)
D: Pd/C (10%), H$_2$, EtOAc, 2HRS rt (90%)
E: 1) 3N.HCl, EtOAc, rt 1HR  2) ION EXCHANGE (AMBERLITE-IRA-400-OH) (66%)
F: 1) Et$_3$N, DMF, 15MIN  2) (BocNH)$_2$CS, DMF, rt 20HRS (36%)
G: 3N.HCl, EtOAc, rt 2HRS (96.4%)

FIG. 6

R = (CH$_2$)$_3$NHBoc    R$^1$ = (CH$_2$)$_3$NH$_2$    R$_2$ = (CH$_2$)$_3$NHC(NBoc)NHBoc

A: H$_2$, Pd/C (10%), EtOH, rt 2HRS (100%)
B: PhCH(OMe)$_2$, DMF, pTSOH CAT, rt 24HRS (75%)
C: KOH (POWDER), THF, 18-CROWN-6 CAT, BnBr, rt 4HRS (82%)
D: 1N.HCl:THF (1:1), rt 12HRS (80%)
E: KOH (POWDER), THF, 18-CROWN-6 CAT, Br(CH$_2$)$_3$NHBoc, rt OVERNIGHT (65%)
F: H$_2$, Pd/C (10%), EtOH rt OVERNIGHT (98%)
G: 1) NaN(TMS)$_2$, THF, -78°C, 1HR 2) CS$_2$, -78°C 1HR 3) MeI -78°C-> rt 1HR (71%)
H: (MeO$_2$P(O)H, DIOXANE, BENZOYL PEROXIDE, REFLUX, 1HR 30MIN (85.3%)
I: 1) 3N.HCl, EtOAc, rt 2HRS  2)ION EXCHANGE (AMBERLITE, IRA-400-OH) (84.5%)
J: 1) Et$_3$N, DMF, rt 15MIN  2) (BocNH)$_2$CS, DMF, rt 20HRS (46.3%)
K: 3N.HCl, EtOAc, rt 2HRS (94.4%)

FIG. 7

R = (CH$_2$)$_3$NHBoc
R$^1$ = (CH$_2$)$_3$NH$_2$
R$^2$ = (CH$_2$)$_3$NHC(NBoc)NHBoc

A: BF$_3$.Et$_2$O, HO(CH$_2$)$_2$OBn, BENZENE, rt 45MIN (46%)
B: NaOMe/MeOH, rt 12HRS (65%)
C: KOH (POWDER), THF, 18-CROWN-6 CAT, Br(CH$_2$)$_3$NHBoc, rt 2HRS (72.6%)
D: Pd/C (10%), H$_2$, EtOAc, 24HRS rt (91.7%)
E: 1) 3N.HCl, EtOAc, rt 1HR  2) ION EXCHANGE (AMBERLITE-IRA-400-OH) (75.9%)
F: 1) Et$_3$N, DMF, 15MIN  2) (BocNH)$_2$CS, DMF, rt 20HRS (50.4%)
G: 3N.HCl, EtOAc, rt 2HRS (92.7%)

5,627,194

ANTI-VIRAL GUANIDINO-SUBSTITUTED COMPOUNDS

This application is a continuation-in-part of Ser. No. 08/153,981 filed Nov. 17, 1993, now abandoned.

FIELD OF THE INVENTION

The present invention relates to anti-viral guanidino-substituted compounds. More particularly, the invention relates to novel guanidino-substituted compounds, and their use in the treatment of herpesvirus infections.

BACKGROUND TO THE INVENTION

Typically, anti-viral agents are modelled to inhibit viral replication within an infected cell. Viral replication may be prevented by down-regulation or inhibition of a protein required in the viral replication pathway, or by interference with the translocation of proteins and viral nucleic acid within the cell. Effective anti-viral agents specifically target steps within the viral replication pathway thereby inhibiting or hindering viral replication within infected host cells while having a minimal cytotoxic effect on the host. Thus, many anti-viral agents are specific inhibitors to virus-specified enzymes and proteins, such as viral DNA and RNA polymerases, virus-specific thymidine kinase and cleavage enzymes for viral capsid protein. Nucleoside analogues, for example, have been developed which target particular enzymes in the viral replication pathway by mimicking a natural substrate of the enzyme.

Adverse toxicity effects exist with the administration of most anti-viral agents, particularly at the dosage levels required to attain effective antiviral chemotherapy, due to a lack of viral specificity. The adverse effects associated with the administration of some anti-viral agents are not as severe as those associated with other agents; nonetheless, such adverse effects do exist. Presently, there are very few anti-viral agents which are considered to be efficacious, i.e. agents having a high level of viral toxicity and a low level of cytotoxicity. accordingly, there is a need to develop anti-viral agents having an effective level of anti-viral activity while exhibiting minimal cytotoxicity, i.e. having a desirable therapeutic index.

It is a general object of the present invention to provide novel guanidino-substituted compounds having anti-viral activity, and compositions containing these compounds.

It is another object of the present invention to provide a method of treating a mammal infected with a herpesvirus.

SUMMARY OF THE INVENTION

It has been discovered that certain guanidino-substituted compounds are effective inhibitors of herpesvirus replication.

The present invention, thus, provides, in one of its aspects, a compound of formula (I):

wherein
X is selected from C, O, N and S;
$R_1$ is selected from H, OH, and linear or branched lower alkyl, lower alkoxy, lower (alkyl-substituted alkoxy), lower alkyl-amine, lower alkyl-thio, hydroxy substituted lower alkoxy, lower alkoxy-alkoxy substituted lower alkoxy, hydroxy substituted lower alkyl-amine, alkoxy substituted lower alkyl-amine and terminally guanidino-substituted linear or branched lower alkyl, lower alkoxy, lower (alkyl-substituted alkoxy), lower alkyl-amine or lower alkyl-thio; and
$R_2$ and $R_3$ are independently selected from linear or branched lower alkyl, lower alkoxy, lower (alkyl-substituted alkoxy) and lower alkyl-amine.

In another aspect, the present invention provides a compound of formula (I) or a salt thereof, wherein
X is selected from C, O, S and N;
$R_1$ is selected from H, OH, and linear or branched lower alkyl, lower alkoxy, lower (alkyl-substituted alkoxy) or lower alkyl-amine, and terminally guanidino-substituted linear or branched lower alkyl, lower alkoxy, lower (alkyl-substituted alkoxy) or lower alkyl-amine; and
$R_2$ and $R_3$ are independently selected from linear or branched lower alkyl, lower alkoxy, lower (alkyl-substituted alkoxy) and lower alkyl-amine.

In yet another aspect, the present invention provides an anti-herpesvirus composition which includes a compound as defined by formula (I), or a salt thereof, in combination with at least one pharmaceutically acceptable carrier.

In a further aspect, the present invention provides a method for treating an anti-herpesvirus infection in a mammal which comprises the step of administering to the infected mammal a therapeutically effective amount of a composition, in a form suitable to treat the herpesvirus infection, which includes a compound according to formula (I), or a salt thereof, in combination with at least one pharmaceutically acceptable carrier.

In yet another aspect of the present invention, there is provided a process of preparing intermediates useful in the synthesis of particular compounds of the invention comprising the step of reacting a compound of the formula with a compound Y—NH—Pr$^1$ in an aprotic solvent in the presence of a Lewis acid to give an intermediate compound of the formula wherein:
Pr$^1$ is an amino protecting group;
Pr$^2$ is a hydroxyl protecting group; and
Y is selected from linear or branched alkyl and linear or branched alkyl substituted with group selected from hydroxyl, alkoxy and guanidino.

Embodiments of the present invention are described in greater detail with reference to the accompanying drawings in which.

BRIEF REFERENCE TO THE DRAWINGS

DETAILED DESCRIPTION OF THE INVENTION AND ITS PREFERRED EMBODIMENTS

The present invention provides novel di-guanidino-substituted compounds having anti-herpesvirus activity. The term "anti-herpesvirus" as used herein refers to those compounds which inhibit replication of a member of the herpesvirus family as determined by conventional cell culture assay, such as the well established plaque reduction assay. In the context of the plaque reduction assay, for example, the anti-herpesvirus nature of a compound in accordance with the present invention is indicated by a reduction in plaque count, or a reduction in plaque size, following treatment of virally infected cells with the given compound, relative to a virally infected, untreated control.

The term "herpesvirus" is meant to encompass viruses which are morphologically similar to herpes simplex viruses and specifically encompasses those viruses which are enveloped, double-stranded DNA viruses. Included within this family of viruses are herpes simplex virus type 1 (HSV-1), herpes simplex virus type 2 (HSV-2), varicella-zoster virus (VZV), Epstein-Barr virus (EBV), cytomegalovirus (CMV), equine herpes virus (EHV) and pseudorabies virus (PRV). Moreover, as one of skill in the art will appreciate, also included within the herpesvirus family are the different isolates and strains of each of the member viruses.

In one of its aspects, the present invention provides a guanidino-substituted compound, or a salt thereof, which is generally defined by formula (I):

wherein

X is selected from C, O, S and N;

$R_1$ is selected from H, OH, and linear or branched lower alkyl, lower alkoxy, lower (alkyl-substituted alkoxy) or lower alkyl-amine, and terminally guanidino-substituted linear or branched lower alkyl, lower alkoxy, lower (alkyl-substituted alkoxy) or lower alkyl-amine; and $R_2$ and $R_3$ are independently selected from linear or branched lower alkyl, lower alkoxy, lower (alkyl-substituted alkoxy) and lower alkyl-amine.

The term "lower alkyl" is used herein to depict alkyl, alkoxy, alkyl-substituted alkoxy and alkylamine groups comprising alkyl chains having from 1–6 carbon atoms.

Further, the term "terminally guanidino-substituted", as used herein with respect to guanidino-substitution on the $R_1$ group, refers to substitution occurring at the carbon atom which is furthest from the ring but which is not a component of a branching chain. So, for example, if $R_1$ is a 2-methylpropyl group, the guanidino-substitution occurs on the terminal carbon of the propyl group and not on the carbon of the methyl side-chain branch.

In one embodiment, $R_1$ is selected from linear or branched lower alkyl, alkoxy, alkyl-substituted alkoxy and alkylamine groups. Branched alkyl groups preferably comprise branched moieties of from 1–3 carbon atoms, i.e. methyl, ethyl or propyl alkyl branches. More preferably, however, the $R_1$ is linear in nature and itself contains from 1–4 carbon atoms, i.e. an alkyl group such as methyl, ethyl, propyl or butyl group, an alkoxy group such as methoxy, ethoxy, propoxy or butoxy group, or in the case of alkyl-substituted alkoxy group, a methoxymethyl, ethoxymethyl or methoxyethyl group, or an alkylamine group such as a methylamine, ethylamine or propylamine group. In a specific preferred embodiment, $R_1$ is an alkoxy group, and preferably a methoxy group.

In another embodiment, $R_1$ represents a terminally guanidino-substituted linear or branched lower alkyl, alkoxy, alkyl-substituted alkoxy or alkylamine group. Preferably the substituted group is a linear group comprising from 1–5 atoms, and more preferably comprising from 2–4 atoms. Thus, for example, the terminally guanidino-substituted group may be an ethyl, propyl or butyl group, or in the case of alkoxy groups, a methoxy, ethoxy or propoxy group, or in the case of alkyl-substituted alkoxy groups, a methoxymethyl, methoxyethyl or an ethoxymethyl group, or in the case of an alkylamine, a methylamine, ethylamine or a propylamine. In a specific preferred embodiment, the terminally guanidino-substituted group is an alkoxy group, preferably a propoxy group.

In accordance with a particular embodiment, compounds of the invention wherein $R_1$ is lower alkylamine or terminally guanidino, hydroxyl or alkoxy substituted lower alkyl-amine may be synthesized from a protected glucal such as tri-O-acetyl-glucal. As shown in the diagram below and described in detail in example 11, a protected glucal is reacted with an N-protected alkyl-amine to give the corresponding N-glucosylated compound wherein Y is alkyl, guanidino substituted alkyl, hydroxy-alkyl or alkoxy-alkyl; $Pr^1$ is a suitable amino protecting group such as Boc or Cbz and $Pr^2$ is a suitable hydroxyl protecting group such as acetyl. The reaction is carried out in an aprotic solvent such as benzene, toluene or dichloromethane in the presence of a Lewis acid such as $SnCl_4$, $AlCl_3$ or $BF_3$ in a temperature range of approximately –40° C. and +20° C. The amino protecting group $Pr^1$ is removed with a suitable reagent allowing the N-glucosylated compound then to be substituted at the 4 and 6 positions, as previously described, ie. alkylation followed by a series of reactions which introduce the desired guanidino-substituted groups at these positions.

$R_2$ and $R_3$ are independently selected from linear or branched lower alkyl, alkoxy, alkyl-substituted alkoxy and alkylamine groups. As set out with respect to branched groups, preferred alkyl branches comprise from 1–3 carbon atoms. More preferably, $R_2$ and $R_3$ are linear groups comprising from 1–6 atoms, e.g. 3–5 atoms. Thus, for example, the $R_2$ and $R_3$ groups, being guanidino-substituted in accordance with FIG. 1, may independently be one of a propyl, butyl or pentyl group, or in the case of alkoxy groups, an ethoxy, propoxy or butoxy group, or in the case of alkyl-substituted alkoxy groups, a methoxymethyl, ethoxymethyl, propoxymethyl or a methoxyethyl group, or in the case of alkylamine groups, an ethylamine, propylamine or butylamine group. In a specific preferred embodiment, $R_2$ and $R_3$ are respectively an alkyl-substituted alkoxy group and an alkoxy group, and preferably $R_2$ and $R_3$ are respectively, propoxymethyl and propoxy groups.

As set out above, X may be any one of a carbon, oxygen, sulfur or nitrogen atom. In the most preferred embodiment, X is an oxygen atom, and the $R_1$, $R_2$ and $R_3$ substituents represent groups that, combined with the oxygen-containing ring, form a substituted sugar backbone, i.e. a substituted pyranose such as a pyranoside. In this regard, particular compounds in accordance with formula (I) include:

4,6-di-O-propylguanidine-2,3-dideoxy-hexoside;
methyl-4-O-ethylguanidine-6-O-propylguanidine-2,3-dideoxy-hexoside;
methyl-4-O-propylguanidine-6-O-ethylguanidine-2,3-dideoxy-hexoside;
methyl-4,6-di-O-ethylguanidine-2,3-dideoxy-hexoside;
methyl-4,6-di-O-propylguanidine-2,3-dideoxy-hexoside;
ethyl-4,6-di-O-ethylguanidine-2,3-dideoxy-hexoside;
ethyl-4,6-di-O-propylguanidine-2,3-dideoxy-hexoside;
ethyl-4,6-di-O-butylguanidine-2,3-dideoxy-hexoside;
propyl-4,6-di-O-ethylguanidine-2,3-dideoxy-hexoside;
propyl-4,6-di-O-propylguanidine-2,3-dideoxy-hexoside;
propyl-4,6-di-O-butylguanidine-2,3-dideoxy-hexoside;
ethylguanidine-4,6-di-O-propylguanidine-2,3-dideoxy-hexoside; and
propylguanidine-4,6-di-O-ethylguanidine-2,3-dideoxy-hexoside.

Figure 1:
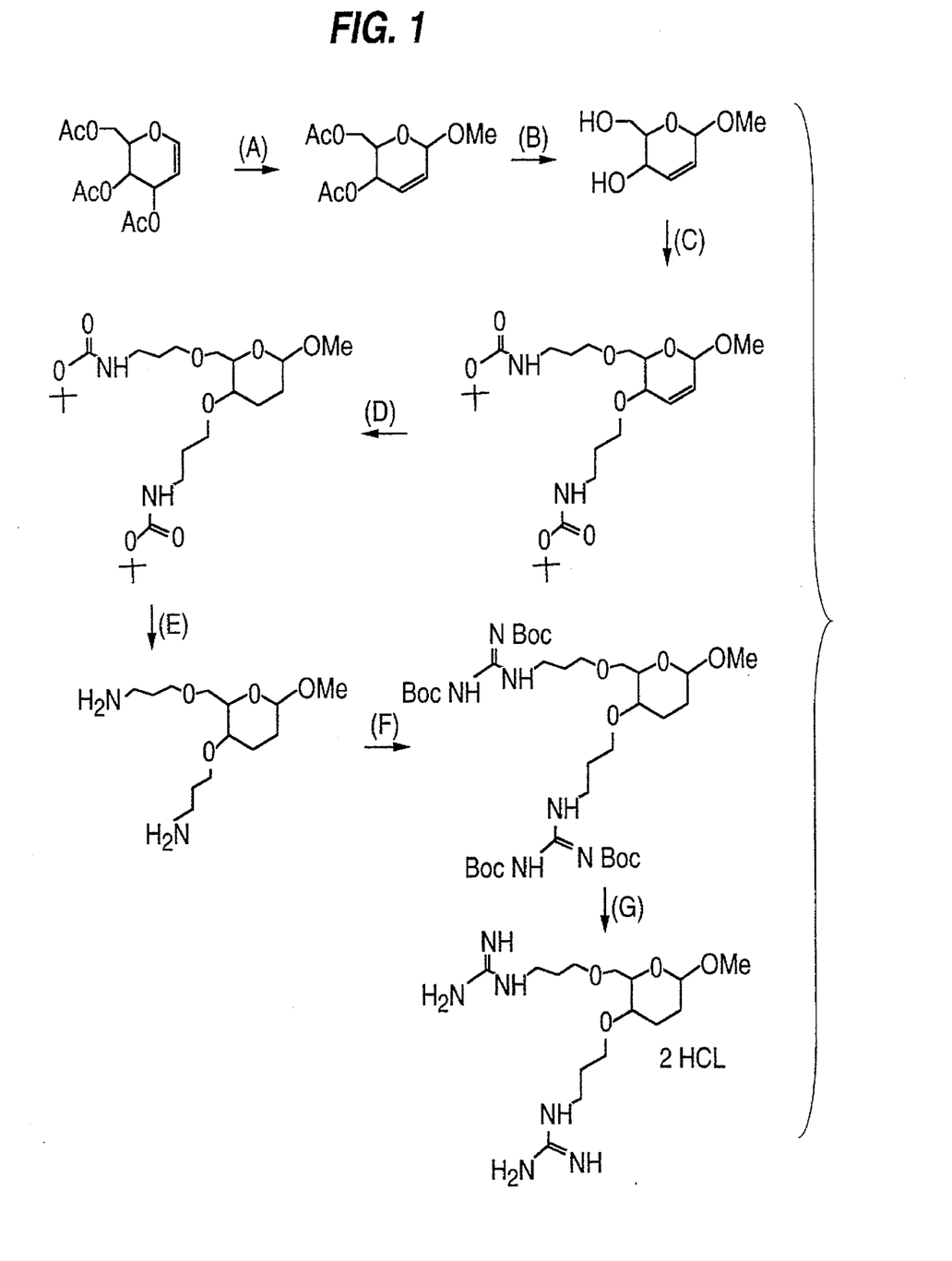
FIG. 1 illustrates the chemical process for preparing a guanidino-substituted compound of the present invention.

Such guanidino-substituted sugar compounds may be made using suitable sugar-based starting materials, such as, for example, a protected glucal. To provide an intermediate which is substituted at position 1, the glucal is reacted with the appropriate alcohol to yield an enopyranoside substituted at position 1 by the deprotonated alcohol. The enopyranoside is then prepared for substitution at positions 4 and 6 by alkylation at these positions, followed by a series of reactions which introduce the desired guanidino-substituted groups at these positions. Included within these process steps is the hydrogenation of the double-bond between $C_2$ and $C_3$ of the enopyranoside to yield a fully saturated hexoside. FIG. 1 illustrates the process steps for the synthesis of the compound, methyl-4,6-di-O-propylguanidine-2,3-dideoxy-hexoside, which is described in detail in the specific examples. One of skill in the art will appreciate that similar process steps can be applied to appropriate starting materials to yield other sugar-based guanidino-substituted compounds, such as propyl-4,6-di-O-propylguanidine-2,3-dideoxy-hexoside, the process for making which is described herein in Example 2.

Moreover, in accordance with further embodiments of the present invention, appropriate heterocyclic starting materials can be used to prepare corresponding substituted piperidine-based compounds in which X is nitrogen, cyclohexane-based compounds in which X is carbon and tetrahydrothiopyran-based compounds in which X is sulfur.

For example, when X is sulfur, 5-thio-D-glucose (Aldrich catalogue, item no. 85,986–9) may be used as a starting material and when X is nitrogen, 1-deoxynojirimycin may be used, the synthesis of which is described in Shankar et al, Tetrahedron Letters, 1993, 34(45):7171. Homologues of the oxygen-containing compounds listed above are prepared from these starting compounds by the steps: 1) protection at the 4 and 6 positions; 2) deoxygenation followed by reduction at positions 2 and 3; 3) oxidation followed by alkylation at position 1 to yield the desired $R_1$ substituent; 4) deprotection at positions 4 and 6 followed by alkylation with N-Boc-aminoalkylbromide, hydrolysis of the N-Boc group to obtain free amino, transformation of the free amino to bis-Boc-guanidino and hydrolysis to yield free guanidino. Steps 1) to 4) may also be used to obtain homologues wherein X is carbon from a suitable starting compound such as quebrachitol (Aldrich catalogue, item no. 36,060-0) or inositol. In this case, a carbon-carbon double bond is introduced at position 5 prior to the protection step 1) by established techniques such as the classical Wittig reaction or organometallic chemistry.

As will be appreciated by one of skill in the art, diastereomers of compounds of the present invention may be separated using techniques well-established in the art, for example, silica gel column chromatography.

Functionally equivalent forms of compounds according to formula (I), such as salts, solvates and hydrates, are also included within the scope of the present invention. Acid addition salts of the present compounds, for example, are salts formed with inorganic acids such as hydrochloric acid, hydrobromic acid, sulfuric acid, nitric acid, phosphoric acid and the like, and organic acids such as acetic acid propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. The preparation of an acid addition salt comprises admixing a compound of formula (I) with the requisite organic or inorganic acid. To convert an acid addition salt of a compound to an alternative salt, an aqueous solution of the salt is treated with base, e.g. sodium carbonate or potassium hydroxide, to liberate the free base which is then extracted using an appropriate solvent such as ether. The free base is then separated from the aqueous portion, dried and treated with the appropriate acid to yield the desired alternative salt compound.

Once a compound according to the present invention has been synthesized, it is desirable to analyze the compound further to ensure its chemical authenticity and purity. Typically, methods of spectroscopy are used to confirm the identity of a compound including, for example, infrared, ultra-violet, nuclear magnetic resonance (NMR), electron spin resonance (ESR), and mass spectroscopy (MS).

Having confirmed the identity of the compound, prior to its use as an anti-viral agent, it must be purified to a "pharmaceutical grade" purity, a term used herein to denote that the compound meets the standards set by the various national bodies which regulate quality of pharmaceutical products. In this regard, it will be appreciated that strict standards of purity may not be required for use of the present compound in vitro or in compositions for use in the veterinary field. Any one of a number of conventional purification procedures may be used to attain the required purity. Reverse phase high-pressure liquid chromatography (RP-HPLC), for example, is one method that is commonly used to purify end products. Fractionation of components in the product mixture is generally accomplished by running a linear gradient, e.g. a mobile phase comprising an increasing percentage of organic solvent such as acetonitrile, in an aqueous buffer usually containing a small amount of an ion-pairing agent such as 0.1% trifluoroacetic acid (TFA), through alkylated silica columns, e.g. $C_4$—, $C_8$—, or $C_{18}$—silica. Alternatively, methods such as ion-exchange chromatography may be used to purify the product.

Purified, pharmaceutical grade guanidino-subsituted compounds of formaul (I), or salts, solvates or hydrates thereof, are used to prepare anti-herpesvirus compositions, according to an aspect of the invention. These compositions comprise at least one carrier and an effective amount of a guanidino-substituted compound, both of which are of pharmaceutical grade as defined above. The expression "an effective amount" is meant to encompass amounts of the anti-viral compound sufficient to prevent or cause a reduction in herpesvirus replication. Such compositions have use in preventing growth of herpesvirus, i.e. by inhibiting viral replication, both in vitro as well as in vivo. In an example of an in vitro application, the anti-herpesvirus composition may be added to cells in culture to prevent undesirable herpesvirus growth which may occur in cell culture. In this application, the present compositions advantegeously exhibit minimal toxicity with respect to the cultured cells. The guanidino-substituted compounds may also be combined to form a crude anti-herpesvirus solution, having utility as a cleaner. Such a cleanser has utility particularly in the laboratory setting for cleansing surfaces which may have been accidentally contaminated with herpesvirus, including counters, floors, cupboard doors, walls, handles and the like.

Anti-herpesvirus compositions for in vivo administration, i.e. for treating infected mammals, are also provided comprising at least one pharmaceutically acceptable carrier and a therapeutically effective amount of a compound in accordance with the invention. In this context, the term "pharmaceutically acceptable" means acceptable for use in the pharmaceutical and veterinary arts. i.e. non-toxic and not adversely effecting the anti-viral activity of the compounds of the present invention. The term "therapeutically effective amount" means an amount of the compound sufficient to cause a reduction in the replication of the herpesvirus target in the infected mammal without adversely effecting the mammal. Such reduction is most properly revealed by assaying virus titer in serum samples derived from the mammal before and after treatment. Further, as used herein, the term "mammal" is meant to encompass humans, domestic animals such as cats, dogs and horses, livestock such as cattle, pigs, goats, and sheep, and non-domesticated mammals that may be in need of anti-herpesvirus treatment.

Pharmaceutically acceptable carriers for inclusion into the present compositions include conventional carriers generally selected for combination with sugar-based drugs such as diluents, excipients and the like. Reference may be made to "Remington's Pharmaceutical Sciences", 17th Ed., Mack Publishing Company, Easton, Penn., 1985, for guidance on drug formulations generally. As will be appreciated, the pharmaceutical carriers used to prepare compositions in accordance with the present invention will depend on the administrable form required to treat a given herpesvirus infection. For example, herpes simplex virus manifest as externally-occurring lesions which may be treated topically; however, some conditions caused by herpesviruses cause internal conditions which are best treated by formulaion which are administrable, for example orally or by injection.

According to one embodiment of the invention, the compounds are formulated for administration by injection, either sub-cutaneously or intravenously, and are accordingly provided as aqueous solutions in sterile and pyrogen-free form and optionally buffered or made isotonic. Thus, the compounds may be administered in distilled water or, more desirably, in saline or 5% dextrose solution. The compounds herein designated as preferred compounds are substantially water-soluble. Water solubility of these and other compounds of the invention may be enhanced, if desired, by incorporating a solubility enhancer, such as cetyltrimethylammonium bromide or chloride. Lyoprotectants, such as mannitol, sucrose or lactose and buffer systems, such as acetate, citrate and phosphate may also be included in the formulation, as may bulking agents such as serum albumin.

Alternatively, the compounds of the present invention may be formulated for administration by routes other than injection. Oral dosage forms, such as tablets, capsules and the like, formulated in accordance with standard pharmaceutical practise, may be employed. Compositions for topical application, such as creams, lotions, or ointments can also be used, as may aerosol inhalable formulations. Creams, lotion and ointment formulations will be useful particularly for application to virally-induced skin lesions. Appropriate triglyceride bases and gels can be used to prepare creams and ointments, which may additionally include surfactants and antimicrobial agents as is conventional.

The present invention provides, in another of its aspects, a method for treating a herpesvirus infection in a mammal which comprises the step of administering to the mammal a pharmaceutical composition, in a form suitable to treat the infection, which comprises a therapeutically effective amount of a compound of the present invention in combination with a pharmaceutically acceptable carrier. According to one embodiment of the invention, the method is applied to the purpose of treating a human patient diagnosed as having a herpesvirus infection. Suitable treatment regimens are those which maintain at the desired site, e.g. in the infected tissue or at a localized skin surface, an amount of the compound sufficient to control herpesvirus replication. The precise dosage sizes appropriate for treatment can readily be established in appropriately controlled trials, and will correspond to an amount of anti-viral compound that affords effective results against herpesvirus replication without causing any harmful or deleterious side effects to the host being treated. It is anticipated that an effective treatment regimen for patients infected with a herpesvirus will involve the systemic administration of dosage sizes in the range of from 1 µg to about 10 mg per kg, e.g., between about 0.01 mg/kg to about 5 mg/kg. It will be appreciated, however, that effective dosage sizes will vary according to the route of administration, the frequency of administration, and, of course, with the particular host to be treated. For example, topical formulations, which remain localized at the infected site, may be administered less frequently than formulations which are administered by injection.

In another aspect of the invention, the present anti-herpesvirus compound may be used as a diagnostic tool. Thus, a biological sample, including for example, blood, urine, or saliva, may be analyzed for the presence of herpesvirus. Specifically, an aliquot of the biological sample to be analyzed is combined with a culture of cells normally killed by the virus, e.g. herpesvirus-sensitive cells such as vero cells, to provide a control. Another aliquot of the biological sample is combined with a culture of the herpesvirus-sensitive cells along with an anti-herpesvirus compound to provide a test sample. The control and test samples are incubated under conditions suitable for cell growth, and are subsequently analyzed for growth of the cells using methods well-established in the art. If the biological sample is virally infected, the cells of the control will be killed by the virus, whereas, in contrast, the cells in the test sample will continue to grow. The presence of the anti-herpesvirus compound will inhibit herpesvirus replication in the test sample thereby allowing growth of the herpesvirus-sensitive cells to continue.

Specific embodiments of the present invention are described in more detail in the following examples which are not to be construed as limiting.

EXAMPLE 1

Synthesis of Methyl-4,6-di-O-propylguanidine-2,3-dideoxy-α,β-D-erythro-hexoside

The compound, methl-4,6-di-O-propylguanidine-2,3-dideoxy-α,β-D-erythro-hexoside was prepared as generally outlined in FIG. 1, and as set out in detail in the following:

A: In a first step to the desired compound, methyl-4,6di-O-acetyl-2,3-dideoxy-hex-2-enopyranoside was prepared as follows.

To a stirred solution of tri-O-acetyl-D-glucal (obtained from Aldrich) (6 g, 22.038 mmol) in dry benzene (20 ml) was added 2.2 mL of methanol and 1.5 ml of boron trifluoride-ether. The reaction mixture was kept under nitrogen for 45 min., and was then washed twice with saturated aqueous sodium bicarbonate and water, and dried with $MgSO_4$. Removal of the solvent yielded methyl-4,6-di-O-acetyl-2,3-dideoxy-α,β-D-erythro-hex-2-enopyranoside in the form of a colorless oil. The product was purified by flash chromatography with an ethyl acetate:hexane (70:30) eluant.

B: The methyl-2,3-dideoxy-α,β-D-erythro-hex-2-enopyranoside intermediate was prepared next. The methyl-4,6-di-O-acetyl-2,3-dideoxy-α,β-D-erythro-hex-2-enopyranoside product of step A (2 g, 8.926 mmol) was stirred in 45 ml of dry methanol. A catalytic amount of sodium methylate (240.9 mg, 4.463 mmol) was added to the stirred solution and stirring at room temperature was continued for 1 hour. The solvent was evaporated and the remaining residue was diluted with ethyl acetate. This mixture was washed twice with brine, dried over $MgSO_4$ and the remaining solvent was evaporatd. The resulting syrup was purified on silica gel using an ethyl acetate/60% hexane eluant to yield as a colorless oil the methyl-2,3-dideoxy-α,β-D-Erythro-hex-2-enopyranoside intermediate.

C: Methyl-4,6-di-O-[1'-N-Boc-propylamine]-2,3-dideoxy-α,β-D-erythro-hex-2-enopyranoside, the third intermediate in the pathway, was prepared by stirring methyl-2,3 -dideoxy-α,β-D-erythro-hex-2-enopyranoside from B) (1 g, 6.248 mmol) in 31 ml of dry tetrahydrofuran, and then adding thereto freshly powdered potassium hydroxide (1.4 g, 24.992 mmol), 18-Crown-6 catalyst (660 mg, 2.499 mmol) and 1-N-Boc-amino propylbromide (3.7 g, 13.745 mmol). The reaction mixture was stirred at room temperature until all starting material was consumed as indicated by TLC (approx. 2 hrs.). The mixture was then diluted with ethyl acetate and washed several times with water. The desired dialkylated intermediate (crude) was obtained following drying of the organic phase over $MgSO_4$, and evaporation of remaining solvent. Purification of the product was conducted on silica gel using ethyl acetate:hexane (50:50) as the eluant.

D: The next intermediate in the pathway, methyl-4,6-di-O-[1'-N-Boc-propylamine]-2,3-dideoxy-α,β-D-erythro-hexoside, was prepared as follows.

The dialkylated product from C) (750 mg, 1.581 mmol) was dissolved in 10 mL of dry ethyl acetate. To the solution was added 50 mg of 10% Pd/c suspended in 5 ml of ethyl acetate. The reaction mixture was stirred at room temperature under a balloon of hydrogen for 2 hours, an then filtered through celite. The filtrate was concentrated and passed through a short column (approx. 2–6 cm in length) of silica gel using an ethyl acetate:hexane (50:50) eluant. The desired hydrogenated product was obtained as a colorless oil.

E: Methyl-4,6-di-O-propylamine-2,3-dideoxy-α,β-D-erythro-hexoside was prepared from the hydrogenated product of D) which was dissolved (170 mg, 0.357 mmol) in 0.5 mL of 3N HCl in ethyl acetate and stirred at room temperature for 2 hours. The solution was removed under vacuum and the resulting oil was triturated with dry ether followed by evaporation. The crude salt was converted to the corresponding free base by passage through an ion exchange resin column (Amberlite IRA-400 OH) using pure methanol as the solvent. The free base was obtained as a white foam.

F: Methyl-4,6-di-O-[di-Boc-propylguanidine]-2,3-dideoxy-α,β-O-erythro-hexoside was then prepared from the product of E) as follows. To a stirred solution of methyl-4,6-di-O-propylamine-2,3-dideoxy-α,β-D-erythro-hexoside (100 mg), 0.359 mmol) in dry DMF (1.5 ml) was added 1.5 ml of dry triethylamine. Following 15 minutes of stirring at room temperature, a solution of di-Boc-thiourea (198.5 mg, 0.719 mmol) in 0.5 mL of dry DMF was added dropwise. The reaction mixture was stirred at room temperature under argon atmosphere for 20 hr. The mixture was then diluted with ethyl acetate, quenched with water and washed twice with brine. The organic phase was dried over $MgSO_4$ and the solvent was evaporated. The crude di-guanidino product was purified on silica gel using ethyl acetate:hexane (40:60) as the eluant to render a white foam.

G: Methyl-4,6-di-O-propylguanidine-2,3-dideoxy-α,β-D-erythro-hexoside dihydrochloride, the desired product, was made as follows:

The methyl-4,6-di-O-[di-Boc-propylguanidine]-2,3-dideoxy-α,β-O-erythro-hexoside product of F (200 mg, 0.263 mmol) was dissolved in 6 ml of 3N-HCl in ethyl acetate, and the reaction mixture was stirred at room temperature for 2 hours. The solution was removed under vacuum and the resulting oil was triturated with dry ether. The solvent was evaporated from the product to yield methyl-4,6-di-O-propylguanidine-2,3-dideoxy-α,β-D-erythro-hexoside in the form of a white solid. The melting point of the product was determined to be 135°–139° C.

EXAMPLE 2

Synthesis of 1,4,6-tri-O-propylguanidine-2,3-dideoxy-hexoside

The synthesis of the compound, 1,4,6-tri-O-propylguanidine-2,3-dideoxy-hexoside was essentially the same as the synthesis outlined in Example 1 for the compound of example 1 with the following exception:

A: To a stirred solution of tri-O-acetyl-D-glucal (6 g, 22.038 mmol) in dry benzene (20 ml) was added 2.2 mL of 1-N-Boc-propanol and 1.5 ml of boron trifluoride-ether. The reaction mixture was kept under nitrogen for 45 min., and was then washed twice with saturated aqueous sodium bicarbonate and water, and dried with $MgSO_4$. Removal of the solvent yield N-boc-O-propyl-4,6-di-O-acetyl-2,3-dideoxy-α,β-D-erythro-hex-2-enopyranoside in the form of a colorless oil.

The remaining steps B through G were conducted as described in Example 1 to yield the product 1,4,6-tri-O-propylguanidine-2,3-dideoxy-hexoside.

EXAMPLE 3

Inhibition of Herpesvirus replication by the compound of example 1

The compound of example 1 was formulated as a 10 mM stock in water for in vitro and cell culture procedures. The stock was then diluted into buffers used for specific assays, or into cell culture media.

The following procedures were then used to determine inhibitory effects of the compound of example 1 on the replication of HSV-1, strain F. First, confluent monolayers of the African green monkey kidney cell line, Vero (ATCC 733-VR CCL 81) in 24 well cell culture plates were pretreated with specified concentrations (0 μM, 0.5 μM, 1 μM, 5 μM, 10 μM, 20 μM and 50 μM) of ALX-19 at 37° C., 5% $CO_2$ for 24 hours. This was accomplished by diluting the stock solution of the test compound in growth medium (10% fetal bovine serum, 100 IU/ml penicillin, 100 μg/ml streptomycin and 0.02 mg/ml gentamicin in Dulbecco's MEM (DMEM)) used to overlay the monolayers.

After pretreatment with the test compound, the monolayers were overlaid with 0.1 ml of diluted virus stock at about 20 pfu/well. Virus was then allowed to absorb for 1 hours at 37° C. The virus inoculum was removed and the monolayers were overlaid with DMEM containing 2% FBS and the specified concentrations of the test compound. Virus was next allowed to replicate for 48 hours and then the monolayers were fixed and stained with a solution of 1% crystal violet in 70% ethanol:formalin:acetic acid (20:2:1). Finally, plaques (each representing a single infectious virus particle or plaque forming unit (PFU) were counted and checked microscopically. The results were as follows:

| CONCENTRATION OF COMPOUND (μM) | PLAQUE NUMBER |
|---|---|
| 50 | — |
| 20 | 1 |
| 10 | 4 |
| 5 | 6 |
| 1 | 16 |
| 0.5 | 18 |
| 0 | 19 |

The $IC_{50}$ was calculated to be 2.6 μM.

The results show that incubation of the cells with the guanidino-substituted compound of example 1 in a concentration of more than 1 μM induces significant reduction in the replication of herpes simplex virus. The therapeutic index of this compound, i.e. the ratio of its cytotoxicity to its viral toxicity, was determined to be 12.29.

EXAMPLE 4

Inhibition of Herpesvirus Replication by the compound of example 2

A procedure similar to that described in Example 3 was conducted to determine the anti-viral activity of the compound of example 2. In the case, however, the concentrations of the test compound used to pretreat the MRC-5 cells were 0 μM, 1 μM, 10 μM, 100 μM and 500 μM, respectively. The following results were obtain on infection and incubation of the treated cells:

| CONCENTRATION OF COMPOUND (μM) | PLAQUE NUMBER |
|---|---|
| 50 | 5 |
| 20 | 6 |
| 10 | 9 |
| 5 | 11 |
| 1 | 16 |
| 0.5 | 18 |
| 0 | 19 |

The $ED_{50}$ was calculated to be 10.51 μM.

The results show that incubation of the cells with the guanidino-substituted compound of example 2 in a concentration of 1 μM or more induces significant reduction in the replication of herpes simplex virus. The therapeutic index of this compound was determined to be >50.

EXAMPLE 5

Synthesis of ethyl-4,6-di-O-propylguanidine-2,3-dideoxy-hexoside

Figure 2:
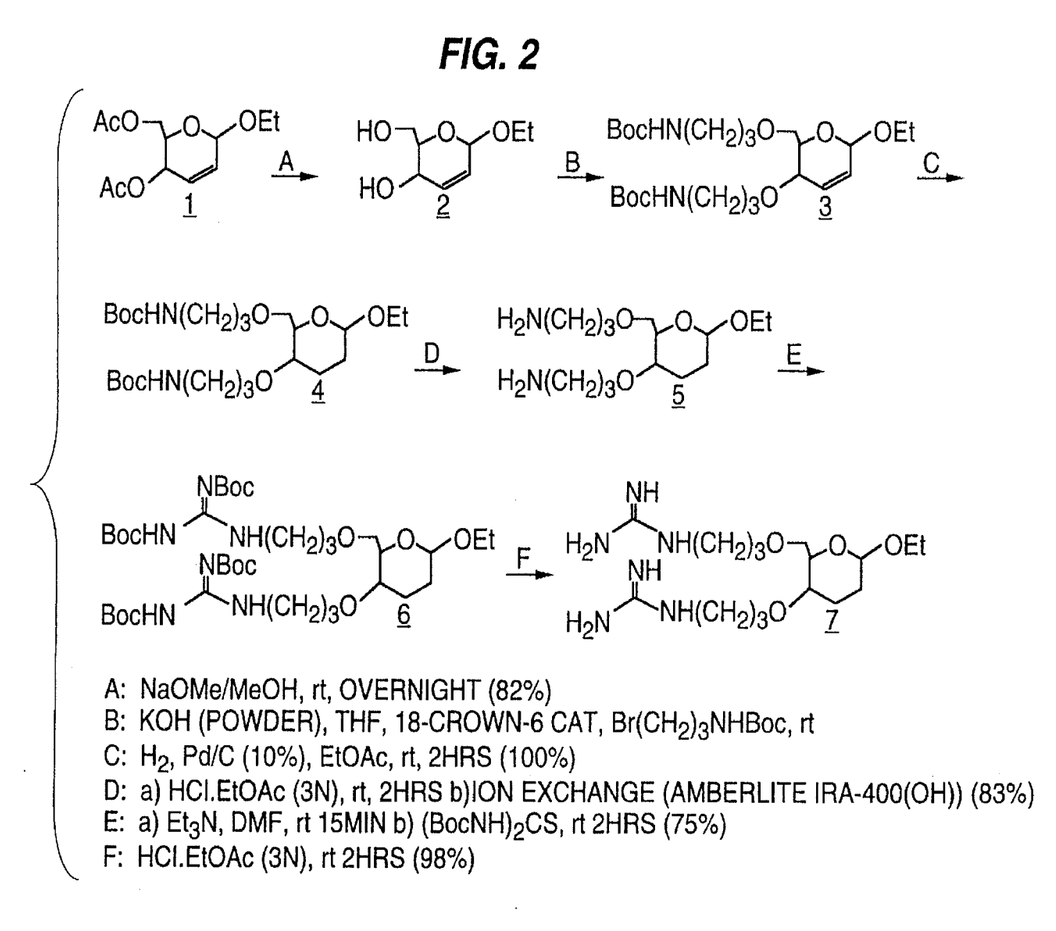
FIGS. 2 to 7 illustrate the chemical processes for preparing guanidino-substituted compounds of examples 5 to 10 respectively.

The compound ethyl-4,6-di-O-propylguanidine-2,3-dideoxy-hexaside was prepared as outlined in the schematic diagram in FIG. 2.

A: Preparation of intermediate (ethyl-2,3-dideoxy-D-erythro-hex-2-enopyranoside) 2

To a stirred solution of ethyl-4,6-di-O-acetyl dideoxy-erythro-2-enopyranoside 1 (2 g, 7.744 mmol) in dry methanol (40 ml), was added a catalytic amount of sodium methylate (168 mg, 3.097 mmol). The reaction mixture was stirred at room temperature for 2 hrs. The solvent was removed and the remaining residue was diluted with ethyl acetate (200 ml). This mixture was washed twice with brine. The organic layer dried over $MgSO_4$ and the remaining solvent was evaporated. The resulting syrup was purified on silica gel column using an ethyl acetate/hexane (60%) as eluant to yield as a white solid (mp 65°–67° C.) the ethyl-2,3-dideoxy-D-erythro-hex-2-enopyranoside 2 (82%).

B: Preparation of intermediate ethyl-4,6-di-O-[1'N-Boc-propylamine]-2,3-dideoxy-D-erythro-hex-2-enopyranoside 3

To a stirred solution of ethyl-2,3-dideoxy-D-erythro-D-hex-2-enopyranoside 2 (770 mg, 4,370 mmol) in dry THF (22 ml), were added succesively freshly powdered potassium hydroxide (980.8 mg, 17.480 mmol), 18-crown-6 catalyst (577.5 mg, 2.185 mmol) and 1-N-Boc-aminopropylbromide (2.63 g, 9.614 mmol). The reaction mixture was stirred at room temperature until all starting material was consumed as indicated by TLC (2 hrs). The mixture was then diluted with ethyl acetate and washed several times with water. The organic layer was dried over $MgSO_4$ after evaporation of the solvent, the crude syrup product was purified on silica gel column using 50% ethyl acetate-hexane as eluant to give as a colorless syrup the ethyl-4,6-di-O-[1'-N-Boc-propylamine]-2,3-dideoxy-D-erythro-hex-2-enopyranoside 3 (65%).

C: Preparation of intermediate ethyl-4,6-di-O-[1'-N-Boc-propylamine]-2,3-dideoxy-D-erythro-hexoside 4

Ethyl-4,6-di-O-[1'-N-Boc-propylamine]-2,3-dideoxy-D-erythro-hex-2-enopyranoside 3 (1 g, 2.046 mmol) was dissolved in 15 ml of ethyl acetate. To the solution was added 80 mg of 10% Pd/C suspended in 5 ml of ethyl acetate. The reaction mixture was stirred at room temperature under a balloon of hydrogen for 2 hrs, and then filtered through celite. The filtrate was concentrated and passed through a short silica gel column using an ethyl acetate hexane (50:50) eluant. The desired hydrogenated compound was obtained as a colorless syrup (approx. 100%).

D: Preparation of intermediate ethyl-4,6-di-O-propylamine-2,3-dideoxy-D-erythro-hexoside 5

Ethyl-4,6-di-O-[1'-N-Boc-propylamine]-2,3-dideoxy-D-erythro-hexoside4(950 mg, 1.936 mmol) was dissolved in 9.6 ml of 3N HCl in ethyl acetate and stirred at room temperature for 2 hrs.

The solution was removed under vacuum and the resulting oil was triturated with dry ether followed by evaporation. The crude salt obtained was converted to the corresponding free base by passage through an ion exchange resin column (Amberlite IRA-400 OH) using pure methanol as solvent to leave the free base 5 as a colorless syrup (83.8%).

E. Preparation of intermediate ethyl-4,6-di-O-[bis-Boc-propylguanidine]-2,3-dideoxy-D-erythro-hexoside 6

To stirred solution of ethyl-4,6-di-O-propylamine-2,3-dideoxy-D-erythro-hexoside 5 (460 mg, 1.504 mmol) in dry DMF (7 ml) was added 2.8 ml of dry triethylamine. After 15 minutes of stirring at room temperature, a solution of bis-Boc-thiourea (962.2 mg, 3.484 mmol) in 2 ml of dry DMF was added dropwise. The reaction mixture was then stirred at room temperature under argon atmosphere for 20 hrs. The mixture was then diluted with ethyl acetate quenched with water and washed twice with brine. The organic layer was dried over $MgSO_4$ and the solvent was evaporated. The crude product was purified on silica gel using ethyl acetate:hexane (40:60) as the eluant to yield a white foam (75%).

F: Preparation of final product ethyl-4,6-di-O-propylguanidine-2,3-dideoxy-hexoside The ethyl-4,6-di-O-[bis-Boc-propylguanidine]-2,3-dideoxy-D erythro-hexoside 6 (110 mg, 0.141 mmol) was dissolved in 1.5 ml of 3N.HCl in ethyl acetate, and the reaction mixture was stirred at room temperature under argon atmosphere for 2 hrs. The solution was then removed under vacuum and the resulting oil was triturated with dry ether. The solvent was evaporated from the product to yield the final product ethyl-4,6-di-O-propylguanidine-2,3-dideoxy-hexoside as a white foam (98%).

EXAMPLE 6

Synthesis of ethyl-4,6-di-O-pentylguanidine-2,3-dideoxy-hexoside

Figure 3:
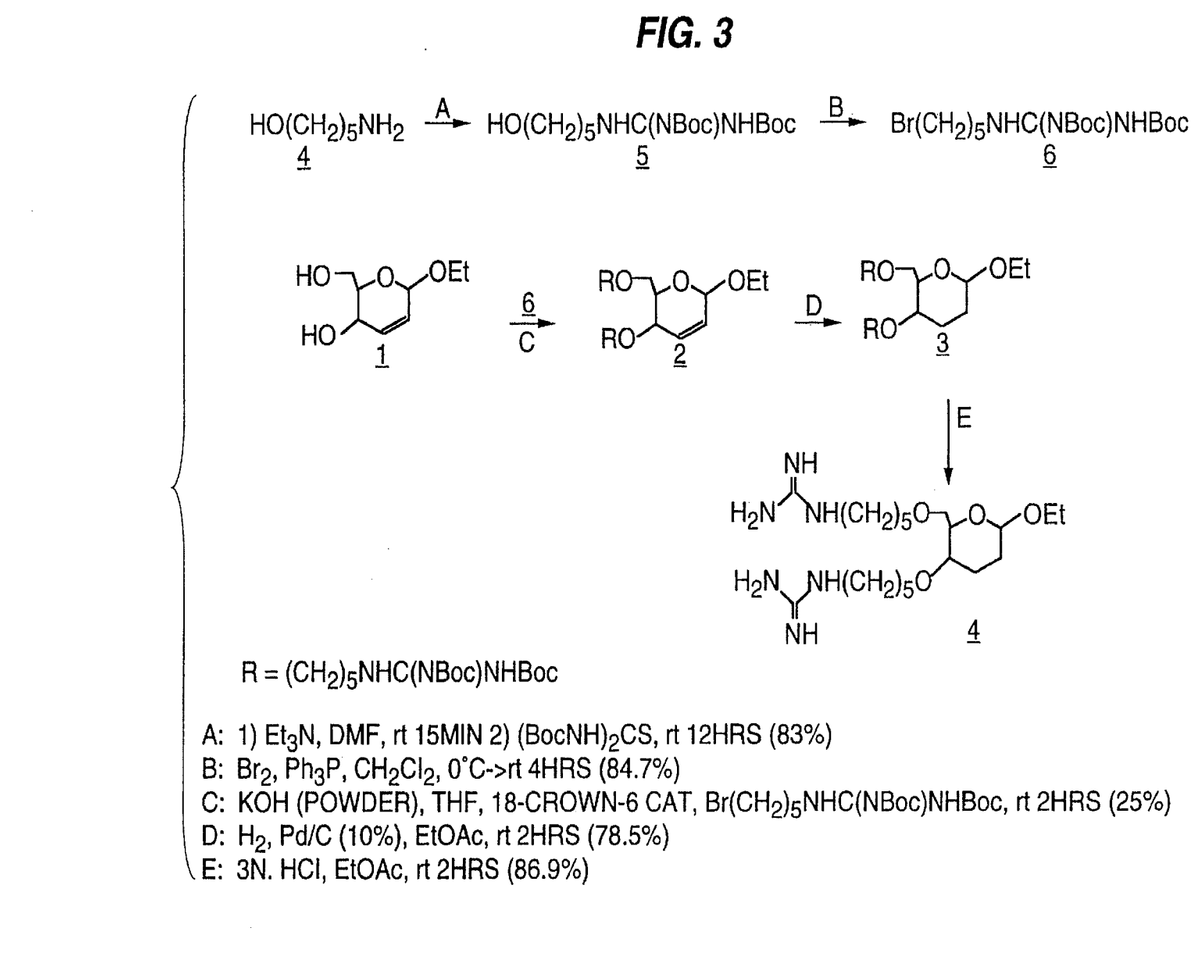

The compound ethyl-4,6-di-O-pentylguanidine-2,3-dideoxy-hexoside was prepared as outlined in the schematic diagram in FIG. 3. The synthesis of which was essentially the same as the synthesis outlined for the compound of example 1.

A: Preparation of intermediate 5-bis-Boc-guanidine-1-pentanol 5

To a stirred solution of 5-amino-1-propanol 4 (934 ml, 9.053 mmol) in dry DMF (23 ml), was added 6.3 ml of dry triethylamine. After 15 minutes of stirring at room temperature, a solution of bis-Boc-thiourea 2.5 g, 9.053 mmol) in 5 ml of dry DMF. The reaction mixture was then stirred at room temperature under argon atmosphere for 4 hrs. The mixture was then diluted with ethylacetate, quenched with water and washed twice with brine. The organic layer was dried over $MgSO_4$ and the solvent was removed. The crude product was purified on silica gel column using ethylacetate:hexane, (40:60), as the eluant, to yield 83% of bis-Boc guanidine compound as a white foam.

B: Preparation of 5-bis-Boc-guanidino-1-pentylbromide 6

To a chilled (0° C.) solution of triphenlphosphine (2.27 g, 8.683 mmol) in dry $CH_2Cl_2$ (60 ml) was added dropwise a solution of bromine (447 µl, 8.683 mmol) in $CH_2Cl_2$ (20 ml). A solution of 5-bis-Boc-guanidino-1-pentylbromide 6 (2 g, 5.789 mmol) in $CH_2Cl_2$ (20 ml) was added dropwise and stirred 4 hrs. at room temperature. Saturated $K_2CO_3$ (3 ml) was added and the mixture was pertitioned between water (50 ml) and ether (50 ml). The organic layer was separated, and the aqueous layer was extracted with ether. The combined organic layers were dried ($MgSO_4$), diluted with an equal volume of hexane, and passed through a short column of silica gel. Removal of the solvent gave 84.7% of bromide 6 as a white powder.

C: Preparation of intermediate ethyl-4,6-di-O-Boc-pentylguanidine-2,3-didoxy-O-hex-2-enopyranoside 2

To a stirred solution of ethyl-2,3-diodexy-D-erythro-hex-2-enopyranoside 1 (143 mg, 0.823 mmol) in dry THF were added successively powdered potassium hydroxide (185 mg, 3.294 mmol), 18-crown-6-catalyst (87 mg, 0.32 mmol) and bis-Boc-guanidinepropylbromide 6 (672 mg 1.647 mmol). The reaction mixture was stirred at room temperature until consumption of total starting material as indicated by TLC (~2 hrs). The mixture was then diluted with ethylacetate and washed several times with water. The organic layer was dried over $MgSO_4$. After evaporation, the crude product was purified on silica gel column using ethylacetate:hexane, (30:70) as the eluant, to afford as a white foam the ethyl-4,6di-O-Boc-pentylguanidine-2,3-dideoxy-O-hex-2-enopyranoside 2 with a 25% yield.

D: Preparation of intermediate ethyl-2,3-dideoxy-O-hexoside 3

Ethyl-4,6-di-O-bis-Boc-pentylguanidine-2,3-dideoxy-O-hex-2-enopyranoside 2 was dissolved in 15 ml of ethyl acetate. To the solution was added 80 mg of 10% Pd/C suspended in 5 ml of ethyl acetate. The reaction mixture was stirred at room temperature under a balloon of hydrogen for 2 hrs, and then filtered through celite. The filtrate was concentrated and passed through a short silica gel column using an ethyl acetate hexane (50:50) eluant. The desired hydrogenated compound was obtained as a colorless syrup (78.5%).

E: Preparation of final product ethyl-4,6-di-O-pentylguanidine-2,3-dideoxy-hexoside 4

Ethyl-4,6-di-O-bis-Boc-pentylguanidine-2,3-dideoxy-O-hexoside 3 dissoved in 3N HCl ethyl acetate and stirred at room temperature for 2 hrs. The solution was removed under vacuum and triturated with dry ether followed by evaporation to give the final product (86.9%).

EXAMPLE 7

Synthesis of isopropyl-4,6-di-O-pentylguanidine-2,3-dideoxy-D-erythro-hexoside

Figure 4:
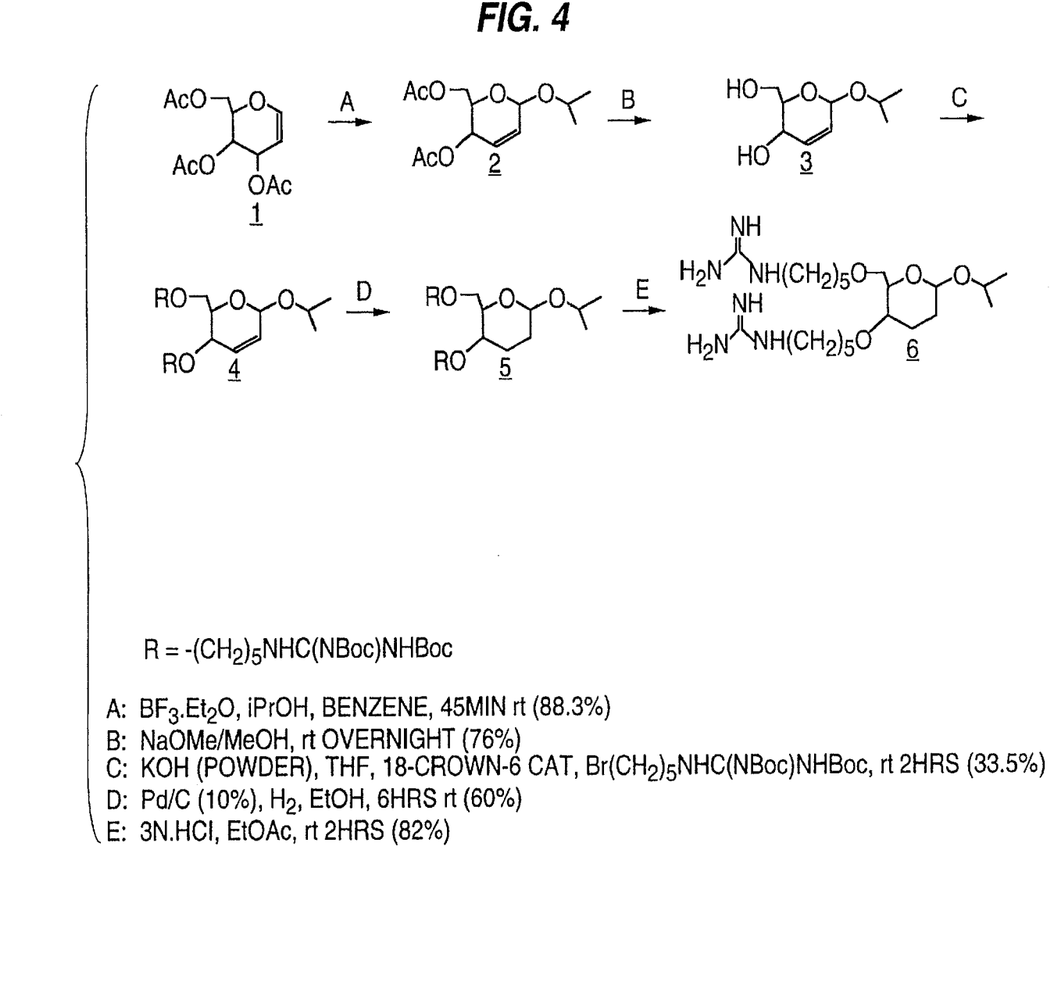

The compound disopropyl-4,6-di-O-pentylguanidine-2,3-dideoxy-D-erythro-hexoside was prepared as outlined in the schematic diagram in FIG. 4. The synthesis was essentially the same as the synthesis described for the compound of example 6 with the exceptions at following steps:

A: Preparation of intermediate isopropyl-4,6-di-O-acetyl-2,3-dideoxy-D-erhtyro-2-enopyranoside To a stirred solution of tri-O-acetyl-D-glucal (6 g, 22.038 mmol) in dry benzene (20 ml) was added (3.3 ml, 44.076 mmol) of 2-propanol. To the solution obtained was added boron trifluoride ether (1.5 ml) The reaction mixture was stirred under argon atmosphere at room temperature for 45 minutes and then diluted with ethyl-acetate and washed twice with saturated aqueous sodium bicarbonate and water. The organic layer was dried (MgSO₄) and evaporated to afford the crude isopropyl-4,6-di-O-acetyl-2,3-dideoxy-D-erythro-2-enopyranoside as a colorless oil, which was purified by flash chromatography using ethyl acetate:hexane (20:80) as eluant (88.3%)

B: Preparation of intermediate isopropyl-2,3-dideoxy-D-erythro-2-enopyranoside 3

The isopropyl-4,6-di-O-acetyl-2,3-dideoxy-D-erythro-2-enopyranoside 2 (5.2 g, 19.097 mmol) was stirred in (100 ml) of dry methanol. To this solution a catalytic amount of sodium methylate (515.8 mg, 9.54 mmol) was added and the stirring was continued at room temperature for overnight. The solvent was evaporated and the remaining residue was diluted with ethyl acetate. This mixture was washed twice with dried (MgSO₄) and evaporated. The resulting syrup was purified on silica gel using ethyl acetate:hexane (60:40) as the eluant to yield isopropyl-2,3-dideoxy-D-erythro-2-enopyranoside 3 as a white powder (76%).

EXAMPLE 8

Figure 5:
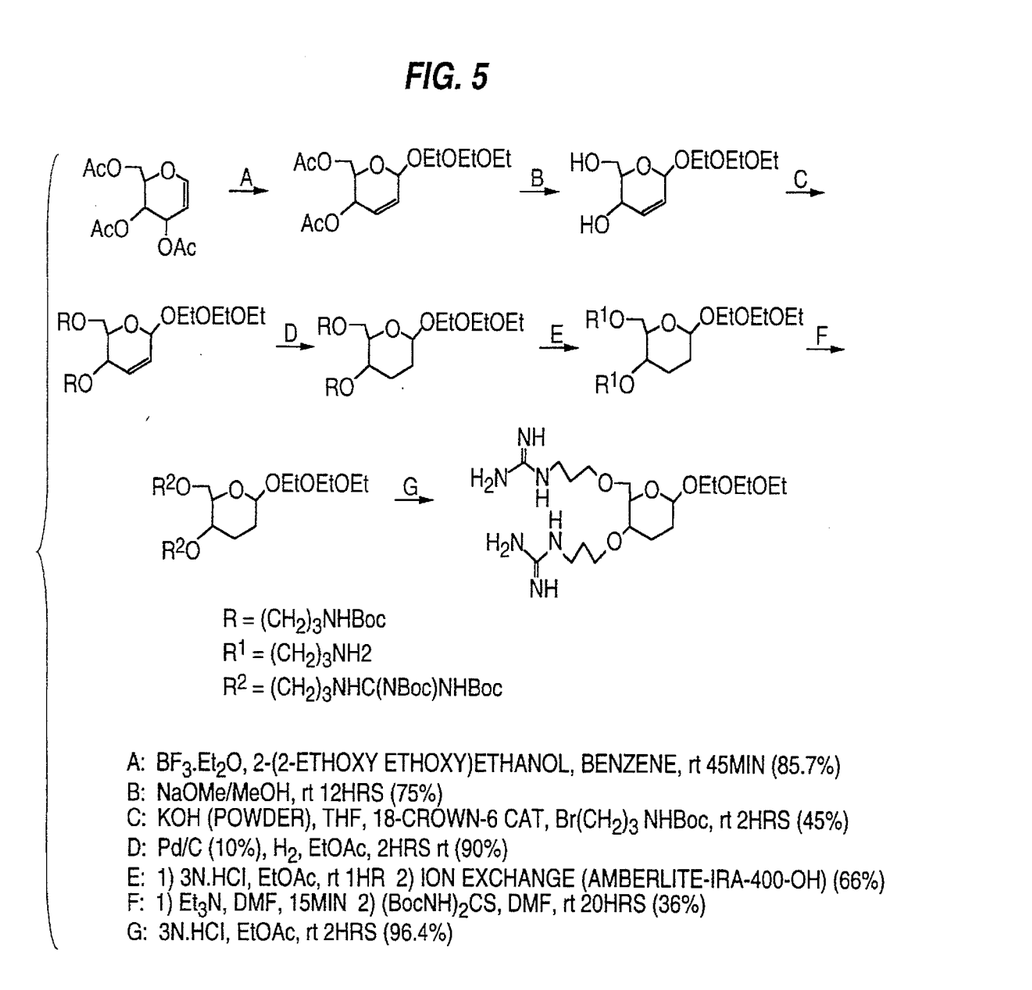

Synthesis of (ethoxy-ethoxy-ethyl)-4,6-di-O-propylguanidine-2,3-dideoxy-d-erythrohexoside The compound (ethoxy-ethoxy-ethyl)-4,6-di-O-propylguanidine-2,3-dideoxy-d-erythro-hexoside was prepared as outlined in the schematic diagram in FIG. 5. The synthesis was essentially the same as the synthesis described for the compound of example 1 with the exception that in the first step A, 2-(2-ethoxy-ethoxy)ethanol was used in place of MeOH to give the intermediate (ethoxy-ethoxy-ethyl)-4,6-di-O-acetyl-2,3-dideoxy-α,β-D-erythro-hex-2-enopyranoside.

EXAMPLE 9

Synthesis of 4,6-di-O-propylguanidine-3-deoxy dihydro-D-glucal

Figure 6:
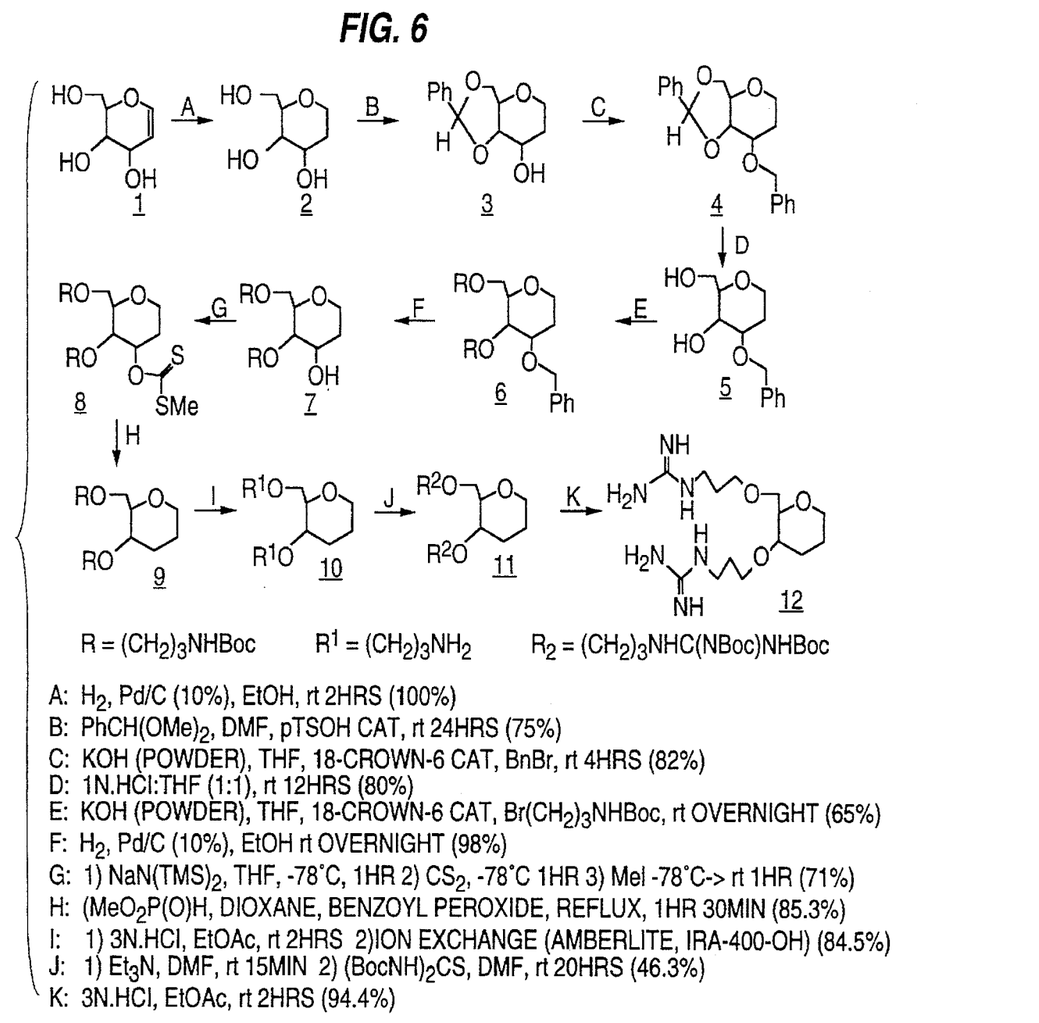

The compounds 4,6-di-O-propylguanidine-3-deoxy dihydro-D-glucal was prepared as outlined in the schematic diagram of FIG. 6.

A: Preparation of intermediate dihydro-D-glucal 2

A mixture of D-glucal 1 (5 g, 34.241 mmol) was stirred in dry ethanol (170 mL) with catalytic amount of Pd/C (10%) (400 mg) at room temperature, under hydrogen atmosphere for 2 hrs. The catalyst was removed by filtration on celite. The solvent was evaporated off and the residue was passed through a short column of silica gel, using EtOAc-MeOH, 95.5 as eluant to give the title compound 2 as a colourless syrup with quantitative yields.

B: Preparation of intermediate 4,6-O-benzylidene dihydro-D-glucal 3

To a mixture of dihydro-D-glucal 2 (3 g, 20.267 mmol), N,N-dimethylformamide (50 ml), and benzaldehyde dimethylacetal (15 ml, 101.334 mmol), was added a catalytic amount of p-toluenesulfonic acid (771 mg, 4.053 mmol). The reaction mixture was stirred at room temperature and under argon atmosphere for 24 hrs. The solution was then diluted with ethyl acetate (200 ml), and quenched with water (100 ml). The aqueous layer was extracted several times with ethyl acetate. The combined organic layers were washed successively with saturated aqueous NaHCO₃, and brine, and dried (MgSO₄) The solvent was removed, and the remaining grade product was chromatographized on silica gel column using ethyl acetate-hexane, (50:50), to give 4,6-0-benzylidene dihydro-D-glucal as a colorless syrup (75% yield).

C: Preparation of 4,6-O-benzylidene-3-benzyl dihydro-D-glucal 4

To a stirred solution of 4,6-0-benzylidene dihydro-D-glucal 4 (1 g, 4.462 mmol) in dry THF (22 ml), were added successively freshly powdered potassium hydroxide (500.7 mg, 8.924 mmol), 18-crown-6 catalyst (589.7 µl, 2.231 mmol), and benzylbromide (636.8 µl, 5.354 mmol). The reaction mixture was stirred at room temperature under argon atmosphere until all starting material was consumed, as indicated by TLC (~1 hr.). The reaction mixture was then diluted with ethyl acetate and quenched with water. The organic layer was dried over MgSO₄ and evaporated, to give the crude product which was purified on silica gel column using ethylacetate:hexane, (10:90) as the eluent, giving 82% yield of, 4,6-O-benzylidene-3-benzyl dihydro-D-glucal as a white solid (mp=75.76° C.).

D: Preparation of intermediate 3-benzyl dihydro-D-glucal 5

To a solution of intermediate 4 (1 g, 3.603 mmol) in THF (154 ml), was added dropwise 1N aqueous HCl solution (15 ml). The mixture reaction was then stirred at room temperature overnight. The mixture was diluted with ethyl acetate and solid sodium chloride was added with stirring. The aqueous layer was extracted twice with ethyl acetate. The combined organic extracts were washed with saturated NaHCO₂ solution and brine, dried (MgSO₄) and evaporated. Purification of the crude product by flash chromatography using ethyl acetate and hexane, (50:50) provided 80% of the expected compound as colorless oil.

E: Preparation of intermediate 4,6-di-O-[1'-N-Boc-propylamine]-3-benzyl dihydro-D-glucal 6

The preparation of 6 (step E) was essentially the same as the step C in example 1

F: Preparation of intermediate 4,6-di-O-[1'-N-Boc-propylamine]-dihydro-D-glucal 7

To a solution of 4,6-di-O-[1'-N-Boc-propylamine]-dihydro-D-glucal 6 (850 mg, 1.537 mmol) in dry ethanol (15 ml) was added 100 mg of Pd/C (10%) as catalyst with stirring. The mixture reaction was stirred at room temperature under hydrogen atmosphere for overnight. The solution was then filtered through celite. The filtrate was concentrated and passed through a short silica gel column using pure ethyl acetate as eluant to lead to desired hydrogenated compound as a colourless syrup, (98% yield).

G: Preparation of intermediate 4,6-di-O-[1'-N-Boc-propylamine]-S-methyl dithiocarbonate-3-dihydro-D-glucal 8

To a stirred solution of the intermediate 6 (700 mg, 1.513 mmol) in dry THF (8 ml) at −78° C., was added dropwise a solution of sodium hexamethyldisilazane (3 ml, 3.000 mmol). The reaction mixture was stirred at −78° C. under argon for one hour. At the same temperature (182 ml, 3.000 mmol of carbon disulfide was added dropwise, and the stirring was continued another hour.

Methyl iodide (100 ml, 3,000 mmol) was then added dropwise, and the reaction was stirred for another hour at room temperature. Ethyl acetate was added and the reaction was quenched with water. The aqueous layer was extracted twice with ethyl acetate. The combined extracts were washed several times with brine, dried and evaporated. Purification of the crude compound by flash chromatography (ethyl acetate:hexane, (40:60)), gave the title S-methyl diothiocarbonate as a colourless oil, with 71% of yield.

H: Preparation of intermediate 4,6-di-O-[1-N-Boc-propylamine]-3-deoxy dihydro-D-glucal 9

To a solution of S-methyl dithiocarbonate intermediate (550 µg, 0.995 mmol) in dry dioxane (6 ml) was added dimethylphosphite (456.3 µl, 4.975 mmol) under argon atmosphere. The reaction mixture was then heated to reflux, and treated at 30 minute intervals with 375 µl portions of a solution of 967.5 mg of benzoylperoxide in 6 ml of dioxane. The reaction was monitored by TLC. When the reaction was complete, the solvent was remove in vacuum and the product was isolated by column chromatography (ethylacetate:hexane, 40:60), to give 65.3% of the deoxygenation compound, as a colorless syrup.

I: Preparation of intermediate ethyl-4,6-di-O-propylamine-2,3-dideoxy-D-erythrohexoside 10

The hydrogenated product of D, 4,6-di-O-[1-N-Boc-propylamine]-3-deoxy dihydro-D-glucal 9, was dissolved 3N HCl in ethyl acetate and stirred at room temperature for 2 hours. The solution was removed under vacuum and the resulting oil was triturated with dry ether followed by evaporation. The crude salt was converted to the corresponding free base by passage through an ion exchange resin column (Amberlite IRA-400 OH) using pure methanol as the solvent to give 4,6-di-O-propylamine-3-deoxydihydro-D-glucal 10 (84.5%)

J: Preparation of intermediate 4,6-di-O-[bis-Boc-propylguanidine]-3-deoxydihydro-D-glucal 11

To a stirred solution of 4,6-di-O-propylamine-3-deoxydihydro-D-glucal 10 in dry DMF (1.5 ml) was added 1.5 ml of dry triethylamine. Following 15 minutes of stirring at room temperature, a solution of di-Boc-thiourea in 0.5 mL of dry DMF was added dropwise. The reaction mixture was stirred at room temperature under argon atmosphere for 20 hr. The mixture was then diluted with ethyl acetate, quenched with water and washed twice with brine. The organic phase was dried over MgSO$_4$ and the solvent was evaporated. The crude di-guanidino product 11 was purified on silica gel using ethyl acetate:hexane (40:60) as the eluant to give a white foam (46.3%)

K: Preparation of final product 4,6-di-O-propylguanidine-3-deoxy dihydro-D-glucal 12 4,6-di-O-[bis-Boc-propylguanidine]-3-deoxydihydro-D-glucal 11 was dissolved in 1.5 ml 3N.HCl in ethyl acetate, and the reaction mixture was stirred at room temperature under argon atmosphere for 2 hrs. The solution was then removed under vacuum and the resulting oil was triturated with dry ether. The solvent was evaporated from the product to yield the final product 4,6-di-O-propylguanidine-3-deoxy dihydro-D-glucal 12 (94.4%).

EXAMPLE 10

Synthesis of hydroxyethyl-4,6-di-O-propylguanidine-2,3-dideoxy-hexoside

Figure 7:
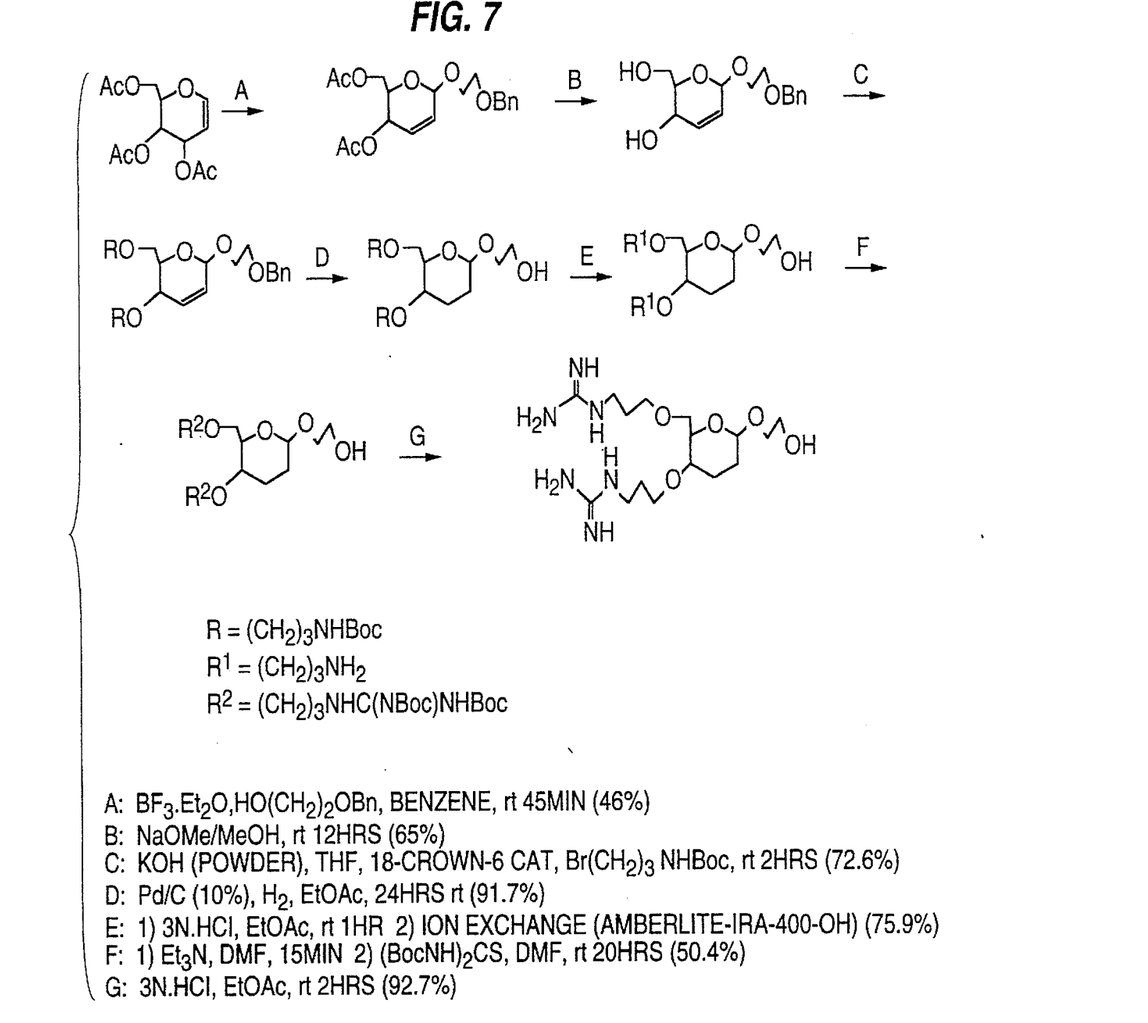

The compound hydroxyethyl-4,6-di-O-propylguanidine-2,3-dideoxy-hexoside was prepared as outlined in the schematic diagram in FIG. 7. The synthesis was essentially the same as the synthesis described for the compound of example 1 with the exception that in the first step A, benzyloxy ethanol was used in place of MeOH to give the intermediate benzyloxy-4,6-di-O-acetyl-2,3-dideoxy-D-hex-2-enopyranoside.

EXAMPLE 11

Preparation of N-glucosylated intermediates

Tri-O-acetyl-D-glucal (200 mg, 0.735 mmol) and CBz-propylamine (284 mg, 1.469 mmol) were dissolved in dichloromethane (3.7 ml) at −10° C. To this solution was added SnCl$_4$ (367 µL of a 1.0M solution in dichloromethane, 367 mmol). The reaction mixture was stirred and allowed to come to 10° C. over a period of one hour. After stirring for an additional four hours at 10° C., the reaction mixture was diluted with dichloromethane (20 ml) and successively washed with water (5 ml), saturated aqueous NaHCO$_3$ (2×5 ml), and brine (5 ml). The organic layer was dried over MgSO$_4$, filtered and concentrated. Flash chromatography using 35% ethyl acetate and 65% hexane as the elutant, afforded the protected N-glucosylated intermediate 1-(N-CBz-isopropylamine)-4,6-di-O-acetyl-1,2,3-trideoxy-enopyranoside as a colourless syrup (106.2 mg, 36% yield).

Further compounds were prepared according to the procedure above with the substitution of the reactant CBz-propylamine with:

Boc-propylamine to give 1-(N-Boc-propylamine)-4,6-di-O-acetyl-1,2,3-trideoxy-enopyranoside (15.3 mg, 6% yield);

CBz-isopropylamine to give 1-(N-CBz-isopropylamine)-4,6-di-O-acetyl-1,2,3-trideoxy-enopyranoside (54.6 mg 18%);

CBz-benzylamine to give 1-(N-CBz-benzylamine)-4,6-di-O-acetyl-1,2,3-trideoxy-enopyranoside (176.7 mg 53%); and Boc-benzylamine to give 1-(N-Boc-benzylamine)-4,6-di-O-acetyl-1,2,3-trideoxy-enopyranoside (96.0 mg 31%).

The following table illustrates results obtained in inhibition and cytotoxicity studies of herpesvirus replication by the compounds exemplified.

| COMPOUND | ED$_{50}$ | TI |
|---|---|---|
| methyl-4,6-di-O-propylguanidine-2,3-dideoxy-hexoside | 2.6 | 12.29 |
| 1,4,6-tri-O-propylguanidine-2,3-dideoxy-hexoside | 10.51 | >50 |
| ethyl-4,6-di-O-propylguanidine-2,3-dideoxy-hexoside | 2.5 | 9.96 |
| ethyl-4,6-di-O-pentylguanidine-2,3-dideoxy-hexoside; | 9.3 | 17.28 |
| isopropyl-4,6-di-O-pentylguanidine-2,3-dideoxy-hexoside | 6.45 | 5.17 |
| 4,6-di-O-propylguanidine-3-deoxy dihydro-D-glucal | ~50 | ~350 |
| hydroxyethyl-4,6-di-O-propylguanidine-2,3-dideoxy-hexoside | 10.78 | 31.22 |
| ethoxyethoxy-ethyl-4,6-di-O-propylguanidine-2,3-dideoxy-hexoside | 10 | >20 |

We claim:
1. A compound of formula (I):

or a salt thereof, wherein

X is selected from C, O, N and S;

R$_1$ is selected from H, OH, and linear or branched lower alkyl, lower alkoxy, lower (alkyl-substituted alkoxy), lower alkyl-amine, lower alkyl-thio, hydroxy substituted lower alkoxy, lower alkoxy-alkoxy substituted lower alkoxy, hydroxy substituted lower alkyl-amine, alkoxy substituted lower alkyl-amine and terminally guanidino-substituted linear or branched lower alkyl, lower alkoxy, lower (alkyl-substituted alkoxy), lower alkyl-amine or lower alkyl-thio; and $R_2$ and $R_3$ are independently selected from linear or branched lower alkylene in which one of the carbon atoms thereof is optionally replaced by an atom selected from nitrogen or oxygen.

2. A compound as defined in claim 1, wherein $R_1$ is selected from H, OH, and linear or branched lower alkyl, lower alkoxy, lower (alkyl-substituted alkoxy), hydroxy substituted lower alkoxy, lower alkoxy-alkoxy substituted lower alkoxy, lower alkyl-amine, and terminally guanidino-substituted linear or branched lower alkyl, lower alkoxy, lower (alkyl-substituted alkoxy) or lower alkyl-amine.

3. A compound of formula (I):

or a salt thereof, wherein

X is oxygen;

$R_1$ is selected from H, OH, and linear or branched lower alkyl, lower alkoxy, lower (alkyl-substituted alkoxy), lower alkyl-amine, lower alkyl-thio, hydroxy substituted lower alkoxy, lower alkoxy-alkoxy substituted lower alkoxy, hydroxy substituted lower alkyl-amine, alkoxy substituted lower alkyl-amine and terminally guanidino-substituted linear or branched lower alkyl, lower alkoxy, lower (alkyl-substituted alkoxy), lower alkyl-amine or lower alkyl-thio; and $R_2$ and $R_3$ are independently selected from linear or branched lower alkylene in which one of the carbon atoms thereof is optionally replaced by an atom selected from nitrogen or oxygen.

4. A compound as defined in claim 3, wherein $R_1$ is a group selected from H, linear lower alkoxy, hydroxy substituted lower alkoxy and lower alkoxy-alkoxy substituted lower alkoxy.

5. A compound as defined in claim 4, wherein $R_1$ is a group selected from methoxy, ethoxy, isopropyloxy, 2-hydroxyethyloxy and ethoxyethoxy-2-ethyloxy.

6. A compound as defined in claim 3, wherein $R_1$ is a terminally guanidino-substituted linear lower alkoxy group.

7. A compound as defined in claim 6, wherein $R_1$ is selected from a terminally guanidino-substituted propoxy group and a terminally guanidino-substituted pentyloxy group.

8. A compound as defined in claim 3, wherein $R_2$ is a linear lower alkylene group in which one of the carbon atoms is replaced by an oxygen atom.

9. A compound as defined in claim 8, wherein $R_2$ is a group selected from propyleneoxymethylene and -O-pentylene.

10. A compound as defined in claim 3, wherein $R_3$ is a linear lower -O-alkylene group.

11. A compound as defined in claim 10, wherein $R_3$ is a group selected from -O-propylene and -O-pentylene.

12. A compound as defined in claim 3, wherein $R_1$ is a group selected from H, linear lower alkoxy, lower (alkyl-substituted alkoxy), hydroxy substituted lower alkoxy, lower alkoxy-alkoxy substituted lower alkoxy and terminally guanidino-substituted linear lower alkoxy group, $R_2$ is a linear, lower alkyl-substituted, lower alkylene group, wherein one of the carbon atoms of the alkylene group is replaced by an oxygen atom, and $R_3$ is a linear lower alkylene group, wherein one of the carbon atoms of the alkylene group is replaced by an oxygen atom.

13. A compound selected from methyl-4,6-di-O-propylguanidine-2,3-dideoxy-hexoside;

1,4,6-tri-O-propylguanidine-2,3-dideoxy-hexoside;

ethyl-4,6-di-O-propylguanidine-2,3-dideoxy-hexoside;

ethyl-4,6-di-O-pentylguanidine-2,3-dideoxy-hexoside;

isopropyl-4,6-di-O-pentylguanidine-2,3-dideoxy-hexoside;

4,6-di-O-propylguanidine-3-deoxy dihydro-D-glucal;

hydroxyethyl-4,6-di-O-propylguanidine-2,3-dideoxy-hexoside; and

α-ethoxyethoxy-ethyl-4,6-di-O-propylguanidine-2,3-dideoxy-hexoside.

14. An anti-herpesvirus composition comprising an effective amount of a compound as defined in claim 2, or a salt thereof, and a pharmaceutically acceptable carrier.

15. A pharmaceutical composition comprising a therapeutically effective amount of a compound as defined in claim 1, or a salt thereof, and a pharmaceutically acceptable carrier.

16. A pharmaceutical composition comprising a therapeutically effective amount of a compound as defined in claim 12, or a salt thereof, and a pharmaceutically acceptable carrier.

17. A pharmaceutical composition comprising a therapeutically effective amount of a compound selected from claim 13 and a pharmaceutically acceptable carrier.

18. A method for treating a mammal having a herpesvirus infection comprising the steps of administering to said mammal a therapeutically effective amount of a compound as defined in claim 1, or a salt thereof, in a form suitable to treat said infection.

19. A method as defined in claim 18, wherein said mammal is infected with a herpes simplex virus.

* * * * *